United States Patent [19]
Yang

[11] Patent Number: 6,129,141
[45] Date of Patent: Oct. 10, 2000

[54] AIR CONDITIONING/PROVIDING SYSTEM DIRECTLY THROUGH NATURAL HEAT PRESERVING MAIN BODY

[76] Inventor: Tai-Her Yang, No. 32 Lane 29, Taipin St., Si-Hu Town, Dzan-Hwa, Taiwan

[21] Appl. No.: 08/192,620

[22] Filed: Feb. 7, 1994

[51] Int. Cl.[7] .................................................. F25D 23/12
[52] U.S. Cl. .............................................................. 165/45
[58] Field of Search ................................................ 165/45

[56] References Cited

U.S. PATENT DOCUMENTS

| | | | |
|---|---|---|---|
| 4,323,113 | 4/1982 | Troyer ........................................ | 165/45 |
| 4,448,238 | 5/1984 | Singleton, Jr. et al. .................. | 165/45 |
| 4,674,561 | 6/1987 | Kelley ........................................ | 165/45 |
| 4,936,110 | 6/1990 | Kückens ................................ | 165/45 X |
| 5,054,297 | 10/1991 | Furuhama .............................. | 165/45 X |

*Primary Examiner*—John Fox
*Attorney, Agent, or Firm*—Bacon & Thomas, LLP

[57] ABSTRACT

This invention provides a primary uniform heater in the natural temperature preserving main body and it is conducted to a room needed to be heated, where the temperature can disperse openly; the temperature is transferred by the heat-conductive fluid by a main pump, or further by a shunt pump; that is, fresh air enters into the primary uniform air-heater through an open filtered inlet, and enter the primay uniform heater of the natural temperature preserving main body and then it is pumped through a transfering tube to a detector in the room needed to be heated. If the conductive tube is long enough to be buried in the natural temperature preserving main body, the primary uniform heater can be omitted and the tube is made of good conductive material's to actuate the function of a primary uniform heating power; a primary filter, such as active carbon filter, tester for harmful gas, and air fresher, can be attached to the inlet and the outlet of the fresh air.

12 Claims, 3 Drawing Sheets

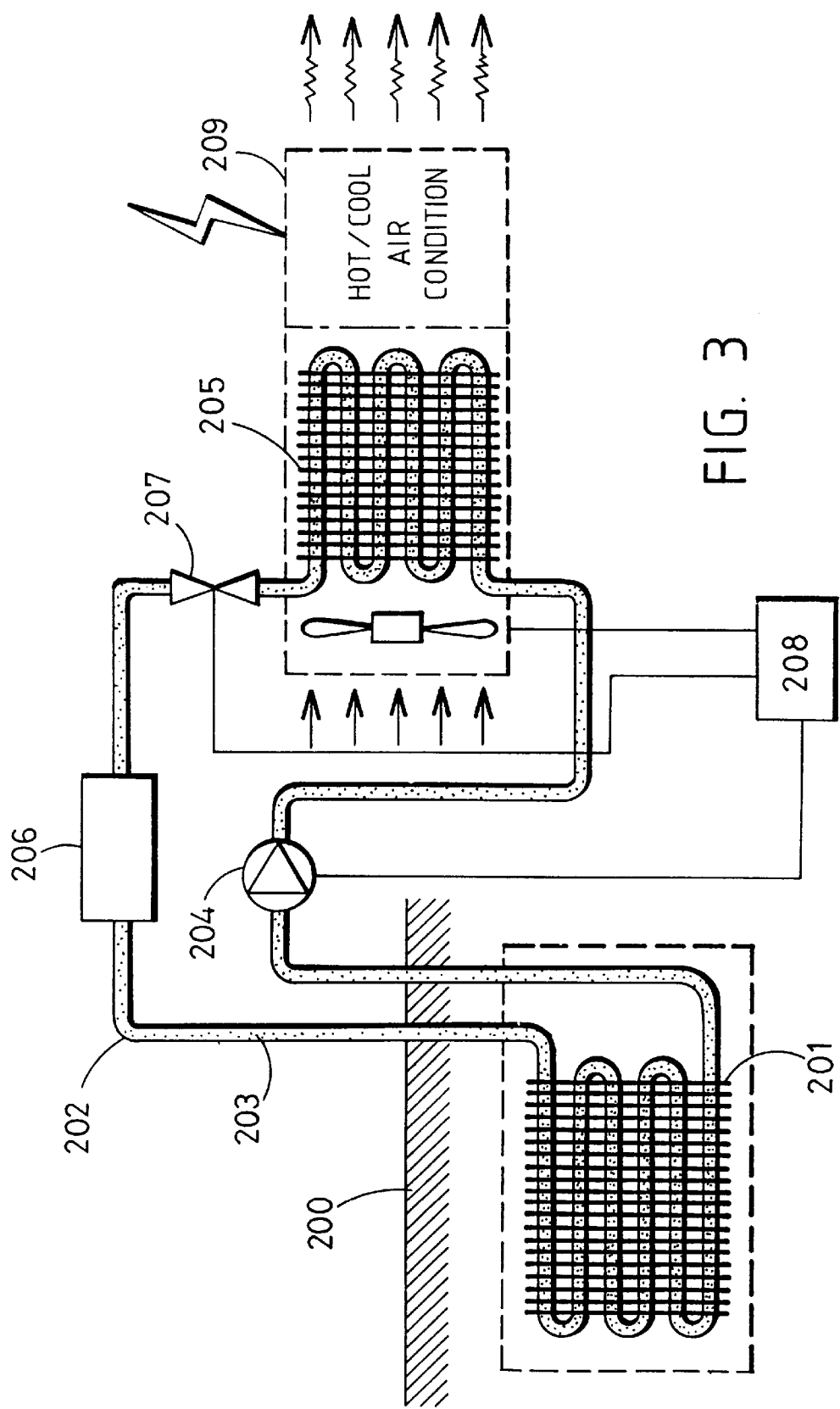

AIR CONDITIONING/PROVIDING SYSTEM DIRECTLY THROUGH NATURAL HEAT PRESERVING MAIN BODY

BACKGROUND OF THE INVENTION

Conventional room temperature regulating system, for example, the air conditioner, uses refrigerant compressor as its main structure for cooling the temperature. Air-heater uses electric power or burns materials for its heat, so it wastes a lot of energy to condition the temperature for a room and produces a great deal of pollution and exhausted heat and materials. Recently, a kind of air conditioning, for example, an ice-preserving type, uses the peak-off electric power to freeze water into ice and then uses the peak power to melt the ice for the air conditioning through a temperature preserving tube. However, this kind of ice-preserving air-conditioner needs (1) a bulky freezer, (2) a well-insulated refrigerator, (3) a large space, (4) input energy; the present invention is unique because it uses the land layers, the land surface, the ponds, lakes, and rivers of the Great Nature as the natural main body for its temperature preserving.

SUMMARY OF THE INVENTION

By means of directly providing the main body's temperature and air for the room to be air-conditioned, the temperature and fresh positive-pressure air of the room will be similar to that of the natural main body. The invention is also provided with the followings:

- as for the room the air is provided to, in addition to the fresh air and regulated temperature, its positive pressure can reduce the dust on the doors and windows, and the polluted air will not enter the room;
- as for the city in a basin, the AIR CONDITIONING/PROVIDING SYSTEM DIRECTLY THROUGH NATURAL HEAT PRESERVING MAIN BODY can provide a positive pressure to make the air in the basin dispersed, convected, and uncontaminated.

BRIEF DESCRIPTION OF THE DRAWINGS

FIG. 3 is a schematic view of the system shown in FIG. 2 provided with a central auxiliary regulating device.

DETAILED DESCRIPTION OF THE PREFERRED EMBODIMENTS

As we know, in winter or in summer, the 10–50 meter depth under the surface layers of the earth is seldom affected by the temperature on the earth surface because its heat capacity is very large. Similarly, sea water, lakes, rivers which are parts of the earth surface can also preserve a constant temperature under a certain depth. In the description of the invention, these parts of earth surface will be known as the natural temperature preserving main body. Because the natural temperature preserving main body has a large heat capacity, in summer its temperature is always lower than that of the air on the surface of the earth; for example, in summer the temperature of river water is usually lower than 15 C. degree; in winter, in the zone of high latitude, when the earth surface temperature is often lower than −20–30 C. degree, the main body will not be lower than 0 C. degree (1–7 C. degree in deep sea). Therefore, when a tube is deviced between the main body and a house to transfer fresh air and regulate the temperature, it becomes an air conditioner which can reduce its cost, its pollution, and its enery exhaust. The present invention, AN AIR CONDITIONING/PROVIDING SYSTEM DIRECTLY THROUGH NATURAL HEAT PRESERVING MAIN BODY, is a device based on the above-mentioned principle, it provides a primary uniform heater in the natural temperature preserving main body and it is conducted to a room needed to be heated, where the temperature can disperse openly. The temperature is transffered by the heat-conductive fluid by a main pump, or further by a shunt pump; that is, fresh air enters into the primary uniform air-heater through an open filtered inlet, and enter the primay uniform heater of the natural temperature preserving main body and then it is pumped through a transfering tube to a detector in the room needed to be heated. If the conductive tube is long enough to be buried in the natural temperature preserving main body, the primary uniform heater can be omitted and the tube is made of good conductive materials to actuate the function of a primary uniform heating power.

A primary filter, such as active carbon filter, tester for harmful gas, and air fresher, can be attached to the inlet and the outlet of the fresh air.

Figure 1:
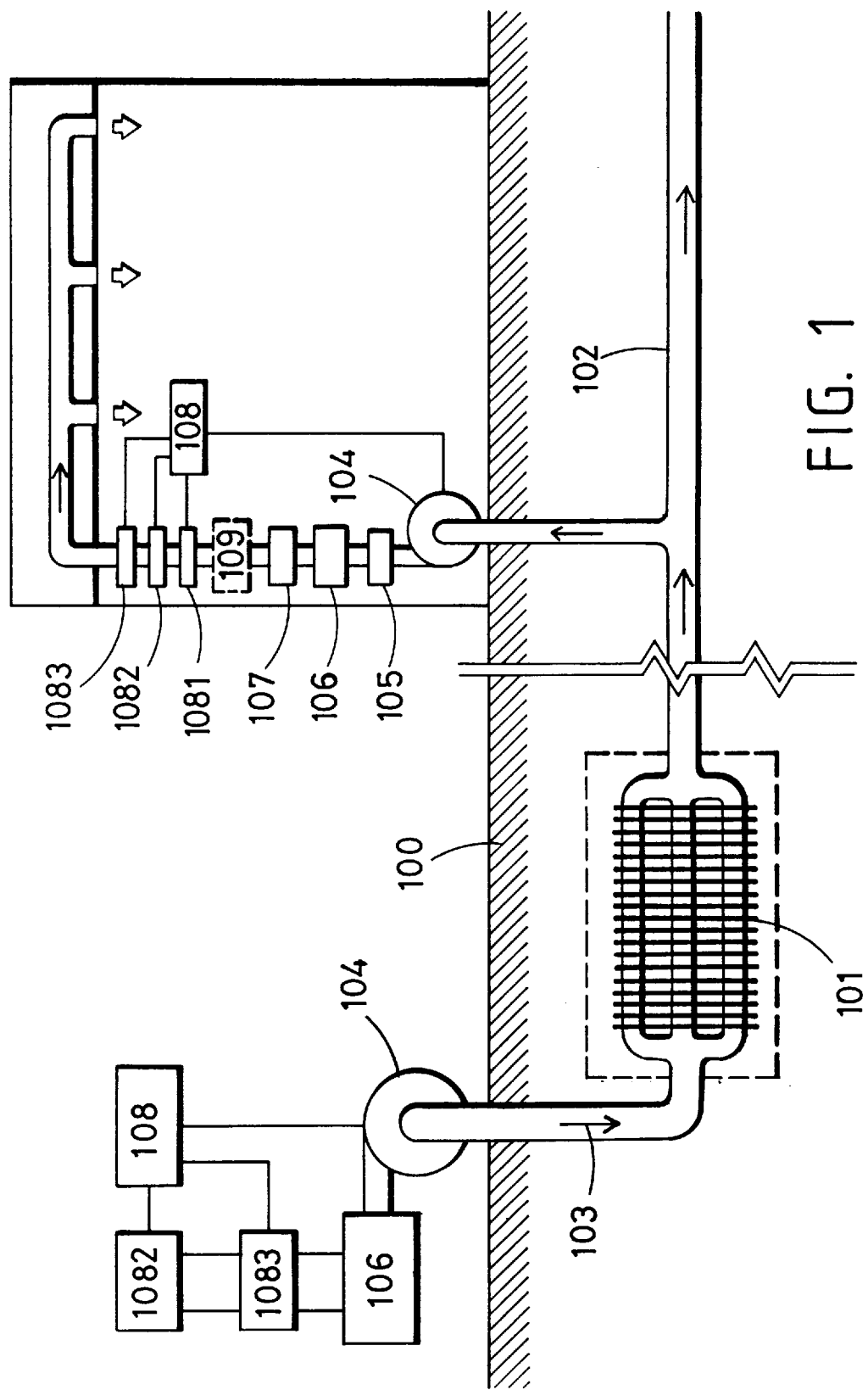
FIG. 1 is a schematic view of the principle of the AIR CONDITIONING/PROVIDING SYSTEM DIRECTLY THROUGH NATURAL HEAT PRESERVING MAIN BODY.

Each embodiment of the invention is illustrated as follows:

As illustrated in FIG. 1, a schematic view of the principle of the AIR CONDITIONING/PROVIDING SYSTEM DIRECTLY THROUGH NATURAL HEAT PRESERVING MAIN BODY, the system comprises:

primary uniform heater 101: it is deviced in the natural temperature preserving main body, and it is made of conductive materials, including a heating tube, at least one inlet and at least one outlet for temperature preserved and transmitted air to float between them so that the temperature of the air from the inlet through the primary uniform heater to the outlet can be more similar to that of the natural temperature preserving main body;

the natural temperature preserving main body 100: it includes the temperature preserving solid or liquid bodies which have larger and stabler temperature preserving capacity than other parts of the nature; for examples, the land layers, land surface, ponds, lakes, rivers, deserts, iceburgs, and oceans; or the emvironment which can perserves fresh air of lower temperature in the valleys or forests;

transmitting pipe line 102: it is used to convey, temperature-preserve and transmit the fresh air; it is made of conductive materials and it passes through a section of the natural temperature preserving body so as to make the temperature of the fresh air it carries almost the same as that of the natural temperature preserving body; when the pipe line passes through temperature-preserving/regulating body (e.g.deep underground), it must be made of conductive materials so that it can regulate the temperature of the fresh air; when it is exposed to the open air, it must be wrapped by or made of insulating materials so that it can insulate heat;

temperature-preserving/transmitting fluid 103: it is used to transmit the temperature of the natural temperature preserving body to the room to be air conditioned; e.t., it uses air as a temperature preserving/transmitting fluid to regulate and transmit temperature and to provide fresh air, too;

air pump 104 driven by electric power or other mechanic forces: it is used to convey fresh air in a transmitting pipe line, including a section or more than one section of pipe lines to pump by a primary pump to preserve and transmit temperature; as for the shorter pipe line, it can be used to pump in/out the air current by means of the temperature difference of the troposphere;

flow gage 105: it is used to calculate the flow of fresh air so that it can be referred to when the subcribers have to pay the charge, this gage is alternative;

filter 106: it is used to prevent the pipe line from being throttled because of long-term use, and it is deviced at the air inlet and outlet; it includes the dust filtering net, the harmful air filter, and filter with active carbon in it;

flow regulating valve 107: when necessary, it is used to regulate the released fresh air flow by manual or mechanic control; it uses a pump to regulate the pumped flow, or the air flow of the fluid outlet valve;

auxiliary regulating relay 109: if the temperature of the primary uniform heater is not sufficient, an auxiliary regulating relay can be applied; it includes the heating devices to gain the temperature by transmitting the temperature of the natural temperature-preserving body, and by the conventional burning, electric heat, or sun energy; or it will reduce the temperature by the input of the conventional temperature reducing device;

control unit 108: it includes the safety protection controller; that is, the input side and each output outlet has a harmful air detecter 1081 so as to send a warning by a siren, cut off the air current, or other methods to deal with an emergency; the harmful air detecter is deviced at the side of input/output port to detect the harmful air in the room; it further includes a temperature inspector 1082 and a fresh air flow gage and indicator 1083 so that it becomes a unit of controlling temperature and regulating air flow.

In addition to being the source of fresh air for regulating/preserving the temperature, the system can be a temperature regulating portion of a conventional temperature regulator and it can be a separator between the temperature differences of middle cascade temperature difference in outer world, it includes:

(1) in winter, when the need for regulating the temperature of the room is higher than the temperature of the fresh air from the natural temperature preserving main body, it will have a pre-heating function;

(2) in summer, when the need for regulating the temperature of the room is lower than the temperature of the fresh air from the natural temperature preserving main body, but when the temperature of the fresh air is lower than the environmental temperature outside the room, it will have a pre-cooling function;

Because the end output of the system has a positive pressure between surrounding environment and space, so in addition to providing and regulating fresh air, it has the following functions:

(A). The system can release fresh air because a positive pressure is built up between indoors and outdoors, and then outdoor floating dust and polluted air are not easy to enter the room;

(B). As to a whole city, an air current source of positive pressure will be built up to disperse outward and this will improve the retaining phenomenon of high sphere air current built up by the land form of a basin.

The system comprises:

fresh air is pumped through a primary uniform heater buried, sunk, hung, or floated under or above the oceans, lakes, ponds, rivers, or artificial pools, which are used as a temperature preserving main body and provide fresh air and temperature regulation for the cabin of a ship and other equipment;

fresh air is pumped through a primary uniform heater buried, sunk, hung, or floated under or above the oceans, lakes, ponds, rivers, or artificial pools, which are used as a temperature preserving main body and provide fresh air and temperature regulation for the rooms of a building on the ground and other equipment:

fresh air is pumped through a primary uniform heater buried under the ground which are used as a temperature preserving main body and provide fresh air and temperature regulation for the rooms of a building and other equipment.

Therefore, the system has the following merits:

1. it only needs the cost of primary equipment at the early stage and the energy for the pumps later on, but it constantly gains fresh air and regulated temperature, so it can save lots of energy; especially when it uses the method of natural convection, it does not need to exhaust any energy at all;

2. it uses the fresh air as a temperature preserving/transmitting fluid in an open space, so it can provide fresh air simultaneously, which is good for people's health and can build up a positive pressure for the outdoor air to prevent polluted air from entering the door, and canbuild up a positive pressure for the whole community or city to reduce the dispersion of polluted air outwardly.

Figure 2:
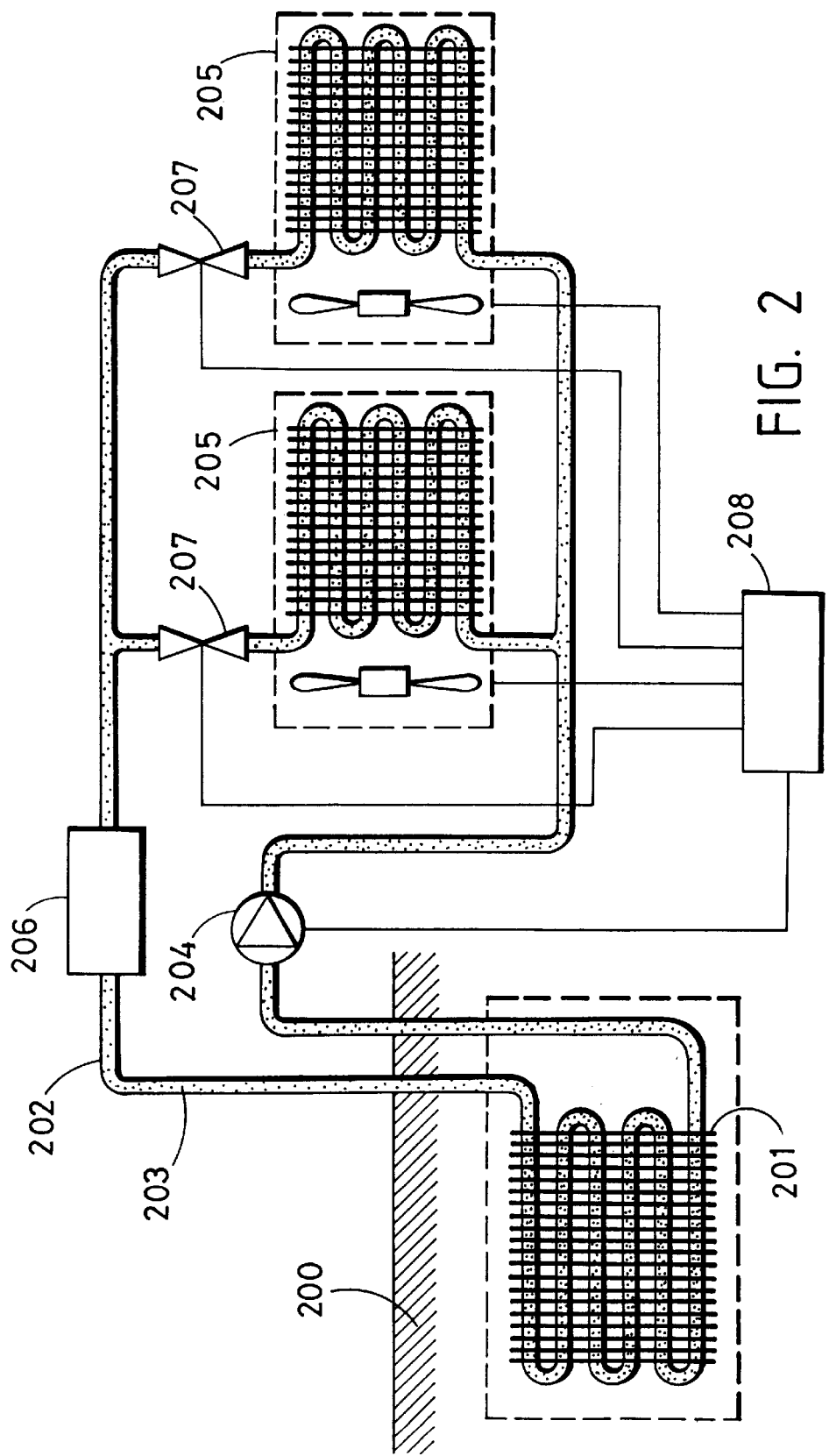
FIG. 2 is a schematic view of the principle of the AIR CONDITIONING/PROVIDING SYSTEM DIRECTLY THROUGH NATURAL HEAT PRESERVING MAIN BODY, of which the air-exhausting system is omitted so as to become a room-temperature regulating system by means of the natural temperature preserving main body.

The embodiment of the invention can also omit the ventilation system, and it can use the space temperature regulating system to transmit and circulate between the natural temperature main body, as shown in FIG. 2, a schematic view of the principle of the AIR CONDITIONING/PROVIDING SYSTEM DIRECTLY THROUGH NATURAL HEAT PRESERVING MAIN BODY, of which the air-exhausting system is omitted so as to become a room-temperature regulating system by means of the natural temperature preserving main body, the embodiment includes:

primary uniform heater 201: it is deviced in the natural temperature preserving main body, and it is made of conductive materials, including a heating tube, at least one inlet and at least one outlet for temperature preserved and transmitted air to flow between them so that the temperature of the air from the inlet through the primary uniform heater to the outlet can be more similar to that of the natural temperature preserving main body;

the natural temperature preserving main body 200: it includes the temperature preserving solid or liquid bodies which have larger and stabler temperature preserving capacity than other parts of the nature; for examples, the land layers, land surface, ponds, lakes, rivers, deserts, iceburgs, and oceans;

transmitting pipe line 202: it is used to convey, temperature-preserve and transmit the fresh air; it is made of conductive materials and it passes through a section of the natural temperature preserving body so as to make the temperature of the fresh air it carries almost the same as that of the natural temperature preserving body; when the pipe line passes through temperature-preserving/regulating body, it must be made of conductive materials so that it can regulate the temperature of the fresh air; when it is exposed to the open air, it must be wrapped by or made of insulated materials so that it can insulate heat;

temperature-preserving/transmitting fluid 203: it is used to transmit the temperature of the natural temperature preserving body to the room to be air conditioned; in the sealed circulating system, it uses water, oil, other liquids, and air as a temperature preserving/transmitting fluid and it directly uses heating pipe made of solid heat conductive materials to regulate and transmit temperature for the solid system;

air pump 204 driven by electric power or other mechanic forces: it is used to convey fresh air in a transmitting pipe line, including a section or more than one section of pipe lines to pump by a primary pump to preserve and transmit temperature; as for the heat pipe line, this device is not necessary, and it can be used to pump in/out the air current by means of the temperature difference of the troposphere;

driven uniform temperature body 205: it is used to transmit the temperature of the natural temperature preserving body to the room to be air conditioned; in the fluid sealed circulating system or, a heating pipe made of heat well-dispersing materials to have a dispersing wing or further have propelling blades;

filter 206: it is used to prevent the pipe line from being throttled because of long-term use, and it is deviced at any position on the sealed and circulating circuit line and on the air inlet and outlet for the open system which uses air as its transmitting fluid;

flow regulating valve 207: when necessary, it is used to regulate the released fresh air flow by manual or mechanic control; it uses a pump to regulate the pumped flow so as to change the driven uniform temperature in the ar conditioned room (or wall), or when the device of the fluid circulating driven uniform temperature and the heat pipe has a uniforn temperature fan, it also can use fanned air flow of the regulating fluid fan to regulate and release the temperature flow;

auxiliary regulating relay 209: if the temperature of the primary uniform heater is not sufficient, an auxiliary regulating relay can be applied; as shown in FIG. 3, a schematic view of the system shown in FIG. 2 provided with a central auxiliary regulating device, it includes the heating devices to gain the temperature by transmitting the temperature of the natural temperature-preserving body, and by the conventional burning, electric heat, or sun energy; or it will reduce the temperature by the input of the conventional temperature reducing device;

control unit 208: it includes the manual, electric, and mechanic controller to control the temperature detecter for the temperature conditioned room and for the natural temperature preserving main body, and the device for presetting the flow.

In addition to being the source of fresh air for regulating/preserving the temperature, the system can be a temperature regulating room of a conventional temperature regulator and it can be a separator between the temperature differences of middle cascade temperature difference in outer world, it includes:

(1) in winter, when the need for regulating the temperature of the room is higher than the temperature of the fresh air from the natural temperature preserving main body, it will have a pre-heating function;

(2) in summer, when the need for regulating the temperature of the room is lower than the temperature of the fresh air from the natural temperature preserving main body, but when the temperature of the fresh air is lower than the environmental temperature outside the room, it will have a pre-cooling function;

Because the system is deviced on the insulated body in the space and the environment to reduce the loss of temperature in the space and to provide an effect of pre-heating or pre-cooling, it can save part of the energy a conventional temperature regulating device needs to exhaust.

As illustrated above, the system comprises:

it has a primary uniform heater buried, sunk, hung, or floated under or above the oceans, lakes, ponds, rivers, or artificial pools, which are used as a temperature preserving main body and provide fresh air and temperature regulation for the rooms of a building on the ground and other equipment;

it has a primary uniform heater buried under the ground which are used as a temperature preserving main body and provide fresh air and temperature regulation for the rooms of a building and other equipment.

Therefore, the system has the following merits: it only needs the cost of primary equipment at the early stage and the energy for the pumps later on, but it constantly gains fresh air and regulated temperature, so it can save lots of energy; especially when it uses the method of natural convection, it does not need to exhaust any energy at all.

The system uses the natural resources and the artificial auxiliary device to provide fresh air and regulate the temperature for a room by means of the natural temperature preserving main body, it uses the fresh air and the heat energy from the nature and feedback them to the nature; when compared with the conventional air conditioner, the present invention does not waste lots of energy, produce no secondary "heat" to harm the public environment, and no CFC to break the ozone sphere, so it is obviously unique.

What is claimed is:

1. A system for conditioning the air in an enclosed area comprising:

a) a naturally occurring temperature preserving main body having a substantially uniform temperature;

b) a primary uniform heat exchanger located in the naturally occurring temperature preserving main body, the primary uniform heat exchanger having a first inlet and a first outlet;

c) first conduit means connected to the inlet of the primary uniform heat exchanger so as to direct a temperature preserving/transmitting fluid into the primary uniform heat exchanger such that the temperature preserving/transmitting fluid assumes a temperature substantially equal to that of the naturally occurring temperature preserving main body wherein the temperature preserving/transmitting fluid comprises air taken from ambient atmosphere externally of the enclosed area;

d) second conduit means connected to the outlet of the primary uniform heat exchanger so as to direct the temperature preserving/transmitting fluid into the enclosed area;

e) a first air pump having an outlet connected to the first conduit means so as to pump fresh air from outside the enclosed area into the first conduit means; and f) a second air pump connected to the second conduit means so as to pump air from the second conduit means into the enclosed area.

2. The system of claim 1 further comprising an air filter connected to the first air pump.

3. The system of claim 1 further comprising an air filter connected to the second air pump.

4. The system of claim 1 further comprising a control unit connected to the first and second air pumps.

5. The system of claim 4 further comprising a flow regulating valve connected to the second air pump so as to control the flow of air into the enclosed area.

6. The system of claim 4 further comprising:
   a) a first temperature sensor connected to the first air pump and to the control unit; and
   b) a first flow gage connected to the first air pump and to the control unit.

7. The system of claim 6 further comprising:
   a) a second temperature sensor connected to the second air pump and to the control unit; and
   b) a second flow gage connected to the second air pump and to the control unit.

8. A system for conditioning the air in an enclosed area comprising:
   a) a naturally occurring temperature preserving main body having a substantially uniform temperature;
   b) a primary uniform heat exchanger located in the naturally occurring temperature preserving main body, the preserving uniform heat exchanger having a first inlet and a first outlet;
   c) a second heat exchanger in heat exchange relationship with the enclosed area, the second heat exchanger having a second inlet and a second outlet;
   d) first conduit means connecting the first inlet and the second outlet;
   e) second conduit means connecting the first outlet and the second inlet so as to form a closed loop system;
   f) a temperature processing/transmitting fluid disposed in the first and second conduit means; and
   g) pump means connected to one of the first and second conduit means so as to circulate the temperature preserving/transmitting fluid through the first and second conduit means, the primary uniform heat exchanger and the second heat exchanger such that the temperature preserving/transmitting fluid passing through the primary uniform heat exchanger assumes a temperature substantially equal to that of the naturally occurring temperature preserving main body.

9. The system of claim 8 wherein the temperature preserving/transmitting fluid comprises air.

10. The system of claim 8 wherein the pump means is connected to the second conduit means and further comprising a filter connected to the first conduit means.

11. The system of claim 8 further comprising control means connected to the pump means.

12. The system of claim 11 further comprising a flow regulating valve connected to the first conduit means and to the control means.

* * * * *